United States Patent [19]

Haschke et al.

[11] 4,054,739
[45] Oct. 18, 1977

[54] PROCESS FOR THE SUBSTITUTION OF CHLORINE ATOMS OF CYANURIC CHLORIDE

[75] Inventors: Heinz Haschke, Weissenstein ob der Drau, Austria; Gerd Schreyer, Hanau, Germany; Werner Schwarze, Frankfurt, Germany; Helmut Suchsland, Rodenbach, Germany

[73] Assignee: Deutsche Gold- Und Silber-Scheideanstalt Vormals Roessler, Frankfurt, Germany

[21] Appl. No.: 656,845

[22] Filed: Feb. 10, 1976

[30] Foreign Application Priority Data

Feb. 12, 1975 Germany .............................. 2505703

[51] Int. Cl.² ........................................ C07D 251/50
[52] U.S. Cl. ..................................... 544/208; 544/204
[58] Field of Search ........................... 260/249.5, 249.8

[56] References Cited

U.S. PATENT DOCUMENTS

| 3,244,712 | 4/1966 | Knusli et al. ............... 260/249.5 X |
| 3,590,040 | 6/1971 | Ferguson et al. ............... 260/249.5 |
| 3,766,182 | 10/1973 | Kuhne et al. ............... 260/249.8 |
| 3,821,220 | 6/1974 | Daugherty et al. ............... 260/249.8 |

FOREIGN PATENT DOCUMENTS

| 1,670,042 | 8/1974 | Germany |
| 1,964,619 | 4/1973 | Germany |

*Primary Examiner*—John M. Ford
*Attorney, Agent, or Firm*—Cushman, Darby & Cushman

[57] ABSTRACT

There is provided a process for the substitution of one or for the successive substitution of two chlorine atoms of cyanuric chloride by one or two amines whch may be the same or different in the presence of an acid binding agent and in the presence of an organic solvent, particularly for the production of 2-alkylamino-4,6-dichloro-, s-triazines and more preferably for the production of 2,4-di-(alkylamino)-6-chloro-s-triazines wherein there is used a 4 to 60 weight % solution or suspension of cyanuric chloride in a mixture of 65 to 85 weight % of one or more aliphatic hydrocarbons or cycloaliphatic hydrocarbons hving 5 to 10 carbon atoms and/or one or more aromatic hydrocarbons and 35 to 15 weight % of one or more ketones having 3 to 8 carbon atoms.

13 Claims, No Drawings

PROCESS FOR THE SUBSTITUTION OF CHLORINE ATOMS OF CYANURIC CHLORIDE

It is known to produce 2,4-dialkylamino-6-chloro-s-triazines by successive reaction of cyanuric chloride with two amines which may be the same or different (i.e. the amine in the first step can be the same or different from that in the second step) in the presence on an acid acceptor and a solvent. As acid acceptors, there can be used for example alkalis, especially sodium hydroxide, and as solvent, for example, toluene, benzene, carbon tetrachloride or the like, see *Ferguson* U.S. Pat. No. 3,590,040. The entire disclosure of said U.S. patent is hereby incorporated by reference and relied upon. In the use of these solvents the reaction takes place with the first amine only relatively slowly, so that in the second step of the reaction the second amine can react with still unreacted cyanuric chloride. This is especially the case when a cyanoalkyl amine is the reacting amine. The result a lower yield and, especialy if the two different amines react in succession, there is considerable byproduct formation. For example, according to the conventional processes, yields of 2-isopropylamino-4-ethyl-amino-6-chloro-s-triazine cannot exceed about 95% of theory, whereby in spite of this relatively low yield, highly impure end products are obtained through the presence of byproducts, i.e., particularly by 2,4-bis-ethylamino or 2,4-bis-isopropylamino-6-chloro-s-triazine, e.g., Ferguson U.S. Pat. No. 3,590,040 and Ferguson German Offenlegungsschrift No. 1,645,948. The entire disclosures of Ferguson U.S. Pat. No. 3,590,040 and German Offenlegungsschrift No. 1,645,948 are hereby incorporated by reference and relied upon. It is also known to use ketones as solvents for the reaction of cyanuric chloride with amines. If the reactions of cyanuric chloride with amines, for example, are carried out in acetone or in acetone/water systems according to Schwarze German Pat. No. 1,670,541 and related Schwarze U.S. Pat. No. 3,505,325, likewise there is only attainable a maximum yield of about 95%; in the production of 2-cyanoalkylamino-4-alkylamino-6-chloro-s-triazines the maximum attainable yields are only about 93% of theory. The entire disclosures of Schwarze German Pat. No. 1,670,541 and Schwarze U.S. Pat. No. 3,505,325 are hereby incorporated by reference and relied upon. In carrying out the corresponding synthesis reaction in such ketones which are only partially miscible with water, as is described in German Auslegeschrift No. 1,695,177 (the entire disclosure of which is hereby incorporated by reference and relied upon) the maximum attainable yields of 2,4-dialkylamino-6-chloro-s-triazines with dissimilar amines in only about 97.5%. For example, in the production of 2-isopropylamino-4-ethylamino-6-chloro-s-triazine, the yield is 97.5% with a product purity of 99.6%. In the synthesis of cyanoalkylamino-amino-chloro-triazines, the yields are substantially poorer.

The byproducts formed in such syntheses besides cause environmental problems, especially because of their toxicity to fish.

It has now been found the above-mentioned disadvantages can be avoided by substitution of one of the chlorine atoms or the successive substitution of two chlorine atoms of cyanuric chloride by the same or different amino groups in the presence of an acid binding agent (acid acceptor) and in the presence of an organic solvent, particularly for the production of 2-alkylamino-4,6-dichloro-s-triazines and more preferably for the production of 2,4-di-(alkylamino)-6-chloro-s-triazines if there is used a 4 to 60 weight % solution or suspension of cyanuric chloride and there is used as the organic solvent a mixture of a. 65 to 85 weight %, preferably 65 to 75 weight % of one or more aliphatic hydrocarbons or cycloaliphatic hydrocarbons having 5 to 10 carbon atoms and/or one or more aromatic hydrocarbons; and, b. 35 to 15 weight %, preferably 35 to 25 weight %, of one or more ketones, e.g., an aliphatic or cycloaliphatic ketone, having 3 to 8 carbon atoms.

The alkyl group or groups of the alkylamino triazine can be substituted as pointed out hereinafter.

In the process of the invention, when reacting cyanuric chloride with a cyanoalkylamine, it is particularly advantageous to use a ketone in the solvent mixture which corresponds to the cyanoalkyl amine used, i.e., which would produce this in the reaction with HCN and $NH_3$.

As aliphatic (and cycloaliphatic) hydrocarbons there can be used, for example, pentane, hexane, heptane, oxtane, nonane, decane and/or their isomers, e.g., isodecane, 2-ethylhexane, isooctane, or 3,3-dimethyl pentane, as well as cyclohexane and as aromatic hydrocarbons benzene, toluene, ethyl benzene and o-, m-, or p-xylene. Examples of ketones include dialkyl ketones and cycloalkyl ketones such as acetone, methyl ethyl ketone, diethyl ketone, methyl n-propyl ketone, methyl isopropyl ketone, methyl n-butyl ketone, methyl isobutyl ketone, ethyl n-amyl ketone, ethyl isoamyl ketone, ethyl n-hexyl ketone, cyclohexanone or cyclopentanone.

Advantageously, there is used a solvent mixture consisting of toluene and acetone in the above-named proportions. Preferred is a mixture of about 70 weight % toluene and 30 weight % acetone. It is especially favorable to start with solution of cyanuric chloride in this type of toluene-acetone mixture.

According to this process, there can be obtained substituted s-triazines in yields above 98% theory. By employing the conditions stated as advantageous or preferred, there can even be attained yields of over 99% of theory. The solvents used can be added in the form of industrial products without a special previous purification. As acid binding agents, there can be added in known manner inorganic bases, oxides, hydroxides, carbonates and bicarbonates of alkali and alkaline earth melts, e.g., sodium hydroxide, potassium hydroxide, calcium hydroxide, barium hydroxide, calcium oxide, barium oxide, sodium oxide, sodium carbonate, potassium carbonate, sodium bicarbonate and potassium bicarbonate. However, there are preferably used the hydroxides, particularly alkali hydroxides. The acid binding agents are preferably used in the form of aqueous solution which contain the acceptor in amounts of 10 to 50 weight %, preferably 20 to 40 weight %, more preferably 20 to 30 weight %.

It is advantageous to proceed in such manner that at the beginning of the dosing of the acid acceptor for completion of the reaction to include with the first amine 1 to 20, preferably 1.5 to 15 weight % of water based on the solvent mixture and that during the acid acceptor addition for reaction with the first amine to maintain a pH range of 2 to 8.5, preferably from 4 to 8, and during the acid acceptor addition for reaction with the second amine to maintain a pH range of 6 to 11.5, preferably from 6 to 11.0 by a correspondingly slow addition of acid acceptor. These pH values are measured in the reaction mixture with commercial glass electrode -single rod-measuring mixture with comparison to an electrode calibration on pure aqueous buffer systems. Before the measurement the glass electrode was calibrated at 20° C. in a pure aqueous buffer solution and then employed directly in the reaction mixture without correction for temperature and medium effect. There was used a single rod-measuring cell of the firm Schott and Gen., Jena; H 63, Abl. Thala-mide, Type H, Zero point pH=7, platinum diaphragm. The named pH value data produce a purely empirical acidity measurement for the given measuring device. They are acidity comparable with the aqueous buffer solutions used for calibration, namely, buffer pH=7: phosphate buffer and buffer pH=9: boric acid—KCl—NaOH.

In carrying out the process of the invention, generally the procedure is to dissolve or suspend the cyanuric chloride in the solvent mixture and then react these solutions or suspensions successively with the same or different amines first to 2-alkylamino-4-dichloro-s-triazines and then to 2,4-di(alkylamino)-6-chloro-s-triazines wherein if desired one or both alkyl groups can have substituents thereon.

As amines for the reaction of the cyanuric chloride according to the invention, there can be used in the first synthesis step, i.e., at least to the formation of the 2-alkylamino-4,6-dichloro-s-triazines, (or substituted 2-alkylamino 4,6-dichloro-s-triazine) 1-cyanoalkylamine-1 such as α-aminoisobutyronitrile (1-cyano-1-methyl-ethylamine-1), 1-cyano-1-methyl-propylamine, 1-cyano-1,2-dimethylpropylamine 1-cyano-1-aminocyclohexane, 1-cyano-1-aminocyclopentane, 1-cyano-1-methyl-methallylamine, 1-cyano-ethylamine-1, cyanomethylamine, 1-cyano-2-methyl-propylamine, 1-cyano-methylthiopropylamine-1, or any of the other cyanoamines described as being useful in the production of halogeno-triazines in German Pat. No. 1,670,520 and Schwarze U.S. Pat. No. 3,505,325 as well as simple and otherwise substituted alkylamines such as methylamine, dimethylamine, ethylamine, cyclohexylamine, di-n-butylamine, methyl ethyl amine, n-propylamine, isopropyl amine, cyclopropyl amine, t-butyl amine, ethyleneimine, diethylamine, n-hexyl amine, n-butyl amine, 3-methoxypropylamine, 2-methylmercaptoethylamine, ethanolamine, allyl amine, 3-ethoxypropylamine, 3-isopropoxypropylamine. If the cyanuric chloride is reacted to form 2-alkylamino-4,6-dichloro-s-triazines or to form 2,4-di (alkylamino) 1-6-chloro-s-triazines with different alkylamino substituents in the 4 or 6-position, of the named amines the 1-cyanoalkylamines are preferred. It is particularly advantageous to employ α-aminoisobutyronitrile for introduction of the first amine substituent into the triazine system. As amines for the further reaction of the 2-alkylamino-4,6-dichloro-s-triazine into the corresponding 2,4-di(alkylamino)-6-chloro-s-triazine there are usually employed simple primary and secondary amines such as methyl amine, dimethyl amine, ethyl amine diethyl amine, n-propyl amine, isopropyl amine, di(isopropyl) amine, n-butyl amine, sec-butyl amine, di-n-butyl amine, t-butyl amine, n-hexyl amine, methyl propyl amine, cyclopropyl amine, cyclohexyl amine or diethyl amine. Ethyl amine and cyclopropyl amine are preferred, especially preferred being ethyl amine.

The process of the invention can be used for example to make any of the 2-amino-4,6-dichloro-s-triazines or 2,4-diamino-6-chloro-s-triazines disclosed in Schwarze U.S. Pat. No. 3,505,375, Ferguson U.S. Pat. No. 3,590,040. Petree U.S. Pat. No. 3,681,337, Saul U.S. Pat. No. 3,681,335, Saul German OS No. 1,670,042, Tandom German OS No. 1,964,619 or Hechenbleikner U.S. Pat. No. 2,476,546 starting from cyanuric chloride and the amines set forth in these U. S. patents and German Offenlegungsschrifts. The amine is added in the reaction of the invention in molar amounts, based on the cyanuric chloride employed; a slight amine excess, maximal 5%, preferably maximal 2% is permitted for the first reaction step, especially if a cyanoalkylamine is used as the amine. Such an excess is also permissible in the second reaction step, independent of the type of amine used. Less than molar amounts of amine per mole of cyanuric chloride employed always lead to a reduction in yield and reduction in purity of the product, and therefore desirably are avoidable.

Advantageously there are added in the reaction in each step per mole of cyanuric chloride 0.98 to 1.05, preferably 0.99 to 1.02 equivalents of the acid acceptors.

During the first reaction step the temperature is advantageously maintained between 0° and 49° C, preferably between 5° and 35° C. Suitably one proceeds so that at the beginning with the addition of the amine the temperature is between 5° and 18° C and towards the end of the addition of the acid acceptor, i.e., when at least 50% of the acid acceptor are added, a somewhat higher temperature is established in the reaction mixture, i.e., up to 40° C, preferably up to 35° C. In the reaction with cyanoalkyl amines in the first reaction step it is suitable to operate at the upper limit of the stated temperature range and in the reaction with simple alkylamines to operate at the lower limit of the stated temperature range. During the second synthesis step it is advantageous to maintain the temperature in the reaction mixture between 40° and 70° C, preferably between 45° and 60° C, particularly between 45° and 55° C.

The 2-alkylamino-4,6-dichloro-s-triazines and 2,4-di(alkylamino)-6-chloro-s-triazines which can be produced according to the process of the invention correspond to the general formula

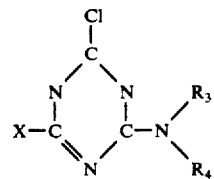

I where X is chlorine or

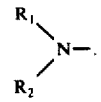

The symbols $R_1$ to $R_4$ in this formula have the following significance wherein by "lower alkyl group" is meant such having 1 to 6 carbon atoms. Preferably the alkyl groups have 1 to 4 carbon atoms $R_1$ and $R_2$ are the same or different and are straight or branch chain lower alkyl, alkenyl, cycloalkyl or methyl cyclopropyl and, in a given case, can be substituted by —OH, —OR$_5$, —SR$_5$, —CN or halogen, e.g., chlorine, bromine or fluorine, where straight or branched R$_5$ is a lower alkyl group.

Preferably one of $R_1$ and $R_2$ is ethyl or cyclopropyl and preferably either $R_1$ or $R_2$ is hydrogen.

$R_3$ and $R_4$ can have the same meaning as $R_1$ and $R_2$. However, preferably $R_3$ is hydrogen and $R_4$ is the group

in which $R_6$ and $R_7$ are the same or different and are straight or branched alkyl or alkenyl groups with 1 to 8 carbon atoms which also can be closed to a 5 to 7 membered ring or can be a cycloalkyl group, preferably methyl, methylcyclopropyl or cyclopropyl, especially methyl and wherein either $R_6$ or $R_7$ can be hydrogen.

The process of the invention is particularly suitable for the production of compositions in which $R_3$ signifies a hydrogen atom and $R_4$ stands for the grouping

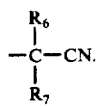

Again, inside this group there is particularly preferred the production of 2-(1'-cyano-1'-methylethylamino)-4-ethylamino-6-chloro-s-triazine. In general, in formula I instead of

there can be a chlorine atom.

The amines which can be used in the invention correspond to the general formulae II and III

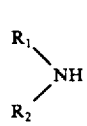 (II)  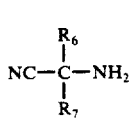 (III)

in which the symbols $R_1$ to $R_7$ have the meanings given in connection with formula I. Their production is known for example from Schwarze German Pat. No. 1,670,528 and related Schwarze U.S. Pat. No. 3,505,325. As a rule there is first introduced the amine of general formula III and then the amine of general formula II.

The cyanoalkylamines, however, can also be added in the form of their equilibrium mixture of ketone cyanohydrin and ammonia dissolved in a stoichiometrical excess of ketone as is described in German Offenlegungsschrift No. 2,416,930 (the entire disclosure of which is hereby incorporated by reference and relied upon). The relatively small amount of water set free in establishing the equilibrium of ketone cyanohydrin and ammonia is not disturbing if an excess of ketone is present.

The compounds obtained according to the process exhibit a biological activity. They particularly have herbicidal activity and also in part are suitable as intermediate products for the production of other active material, particularly herbicide. By substitution of the residual chlorine atom in these compounds by mercapto, alkoxy or alkylamino groups there are producible in particularly high yield and purity further industrially valuble products, for example herbicides, rubber auxiliary agents, etc.

The following comparison and illustrative examples serve to further explain the invention.

Unless otherwise indicated all parts and percentages are by weight.

COMPARISON EXAMPLE 1

There were placed in a 2 liter five necked flask equipped with a mechanical stirrer, reflux condenser, cold finger (bed with cooling brine of minus 5° C), glass electrode (= single rod-measuring cell of the firm Schott and Gen., H63,ABl. Thalamid, Type H, Zero point pH=7, platinum-diaphragm), dropping in measurer and thermometer 830 grams of industrial acetone (having a water content of 0.2%). There were introduced into the acetone with stirring within 5 minutes 92.2 grams (= 0.5 mole) of powdered cyanuric chloride (identified hereinafter sometimes as "Cy"; at least 99% pure; melting point 145.5° to 146° C). While the cyanuric chloride dissolved in the acetone to form a 10 weight % solution the mixture was cooled to 0° C. As soon as this temperature was reached there was begun the dropping in of freshly distilled α-aminoisobutyronitrile (="AIBN"). In all there were added 43.8 grams of 98% (balanced water) AIBN, i.e., 0.51 mole (mole ratio Cy : AIBN = 1:1.02) inside 20 minutes. Thereupon there were immediately added 14 ml of distilled water; subsequently there was begun the dropping in of 25 weight % aqueous NaOH, namely so that inside 4.7 hours there were added a total of 80 grams (i.e., 0.5 mole) of 25% NaOH, whereby the NaOH addition took place in such manner that pH value in the reaction mixture was increased from 4.6 at the beginning to a maximum of 7.8 toward the end of the time of addition. Twenty minutes after beginning the addition of NaOH there was also added to the reaction mixture a further 120 ml of water.

Two hours after the beginning of the NaOH addition up to a total addition of sodium hydroxide lye of 80 grams the temperature of the reaction mixture was increased to 20° C. After the NaOH addition took place there were added within 20 minutes 46.4 grams of 49% aqueous ethyl amine (="ETNH₂"; 0.5 mole). Thereupon the reaction mixture was heated to 50° C and there was added further 25% aqueous sodium hydroxide lye, namely so that again 80 grams of NaOH solution were added within 4.7 hours with a slow pH change from pH=7.1 up to pH=10.4 and this last pH was retained until the entire amount of sodium hydroxide solution was added.

The thus obtained acetonic suspension was now divided into two exactly equal halves. The first half was designated solution "A" and was evaporated to dryness on a rotary evaporator in a water jet vacuum. There were obtained 87 grams of a mixture consisting essentially of 29 grams (about 34%) of sodium chloride, 54 grams (i.e., about 63% corresponding to 0.23 mole, i.e., only about 90% of theory) 2-(1'-cyano-1'-methyethylamino)-4-ethylamino-6-chloro-s-triazine and 3 grams of cyanuric acid. The residue was found to be a mixture of 2-(1'-cyano-1'-methylethylamino)-4-amino-6-chloro-s-triazine and 2,4-diethylamino-6-chloro-s-triazine which were contained in the product in an amount of about 1.8% based on the 54 grams of the desired triazine derivative.

The second half of the aqueous acetonic suspension, designated solution "B", was greatly diluted with water. Thereupon a white precipitate fell out. This was filtered off and the filtrate diluted with more water until no more precipitate formed. The total precipitate filtered off was dried in a vacuum (12 mm Hg) at 60° C. There were obtained 5.5 grams of a white powder which comprised 95% of the desired 2-(1'-cyano-1'-methylethylamino)-4-ethylamino-6-chloro-s-triazine. The remainder was found to be cyanuric acid, 2-(1'-cyano-1'-methylethylamino)-4-amino-6-chloro-s-triazine, 2,4-diethylamino-6-chloro-s-triazine and a residue which was not further identified, however, in contrast to the desired product was a material poorly soluble in methylene chloride. The total yield of 2-(1'-cyano-1'-methylethylamino)-4-ethylamino-6-chloro-s-triazine therefore according to this method was only 87% of theory.

If the reaction is carried out in the same manner with the only difference that the first reaction step is not run at 0° C but instead is run at 10° C or at still higher temperatures while there is practically no 2,4-diethylamino-6-chloro-s-triazine in the end product the yield of 2-(1'-cyano-1'-methylethylamino)-4-ethylamino-6-chloro-s-triazine is reduced to below 80-85% of theory. Besides the portion of cyanuric acid formed is increased as is the byproduct 2-(1'-cyano-1'-methyl-ethylamino)-4-amino-6-chloro-s-triazine.

COMPARISON EXAMPLE 2

There were placed in the apparatus described in Comparison Example 1, 830 grams of toluene. There were suspended therein with stirring at room temperature 92.2 grams (=0.5 mole) of powdered cyanuric chloride (at least 99% pure, melting point 145.5°-146° C). Stirring was continued at room temperature until the cyanuric chloride was substantially dissolved. Then it was cooled to 10° C. Thereupon there were added 43.8 grams of 98% α-aminoisobutyronitrile within 20 minutes. Then there were immediately added 14 ml of water and subsequently there was begun the dropping in of 80 grams of 25% aqueous NaOH. The NaOH addition took place again similarly within 4.7 hours as described in comparison Example 1. Twenty minutes after the beginning of the addition of the aqueous sodium hydroxide there was added 120 ml of water; during the last 2.7 hours of the NaOH addition the reaction mixture was held at 30° C. The NaOH addition took place in the same pH interval as is given in Comparison Example 1. Then there were added 46.4 grams of 49% aqueous ethylamine within 20 minutes and heating thereby to 50° C. At this temperature there were added a further 80 grams of 25% aqueous NaOH solution and namely in such manner that the total amount of lye was added in a time span of 4.7 hours under consideration of a pH span of 7.1 to 10.4. The thus obtained 3-phase suspension consisted essentially of an aqueous NaCl-containing phase, an organic (toluenic) phase containing dissolved at 20° C about 4 weight % of 2-(1'-cyano-1'-methylethylamino)-4-ethylamino-6-chloro-s-triazine and from crystals of the same, crude cyanoalkylamino-chlorotriazine. They were filtered.

The organic (upper) phase in the filtrate was separated and subsequently evaporated to dryness at the water jet vacuum. In all there were obtained 113 grams of dry, yellow-colored product which according to the analysis (thin layer and gas chromatography, as well as IR-spectroscopy) had the following composition: 79 weight % of the desired 2-(1'-cyano-1'-methylethylamino)-4-ethylamino-6-chloro-s-triazine, besides 15 weight % of 2,4-diethylamino-6-chloro-s-triazine, 5-weight % 2-(1'-cyano-1'-methylethylamino)-4,6-dichloro-s-triazine, about 1 weight % of 2-(1'-cyano-1'-methylethylamino)-4-amino-6-chloro-s-triazine and traces of not further identified color formers or by products or decomposition products. The amount of product obtained corresponds to a total yield of all the named materials of about 97% of theory based on the cyanuric chloride employed. The yield of 2-(1'-cyano-1'-methylethylamino)-4-ethylamino-6-chloro-s-triazine (calculated from the content in the mixture of materials obtained) amounted to only about 94% of theory.

COMPARISON EXAMPLE 3

In an apparatus as described in Comparison Example 1 there was carried out a further change while maintaining all of the operation details described in Comparison Example 2. However, instead of toluene there was used a mixture of 747 grams of toluene and 83 grams of acetone, corresponding to a toluene-acetone-mixture in the ratio 90:10 weight % as the starting solution.

The 3-phase suspension resulting from the end of the second NaOH addition at 50° C (aqueous-acetonic NaCl containing phase, toluenic-acetonic-triazine-containing phase and solid triazine-phase) was filtered after dilution with 1 liter of water. The toluenic-acetonic phase was separated from the filtrate and evaporated to dryness in a vacuum. The thus obtained triazine residue was combined with the filtered off triazine, washed with a little cold water and dried in a vacuum at 60° C. There were obtained 110.6 grams of a white powder which according to the analysis contained 85.5 weight % of the desired 2-(1'-cyano-1'-methylethylamino)-4-ethylamino-6-chloro-s-triazine and besides still contained 10 weight % of 2,4-diamino-6-chloro-s-triazine, 3 weight % of 2-(1'-cyano-1'-methylethylamino)-4,6-dichloro-s-triazine and 1.5 weight % of 2-(1'-cyano-1'-methylethylamino)-4-amino-6-chloro-s-triazine. Based on the content of the desired triazine in the product obtained the yield was about 78.6% of theory.

EXAMPLE 1

There were placed in the same apparatus described in Comparison Example 1, 830 grams of a mixture of 65 weight % industrial toluene and 35 weight % industrial acetone (about 0.2% water content). There were introduced into this mixture with stirring within about 5 minutes 92.2 grams (=0.5 mole) of powdered cyanuric chloride (at least 99% pure, melting point; 145.5°-146° C). While the cyanuric chloride dissolved in the solvent mixture to form a 10 weight % solution the mixture was cooled to 10° C. As soon as this temperature was reached there was begun the dropping in of freshly distilled α-aminoisobutyronitrile. In all there were added 43.8 grams of 98% (balance water) α-aminoisobutyronitrile, i.e., 0.51 mole (mole ratio cyanuric chloride; α-aminoisobutyronitrile=1:1.02) within 20 minutes. Then there immediately were added 14 ml of distilled water; subsequently there was begun the dropping in of 25 weight % NaOH, namely at such a rate that 80 grams were suitably added within 4.7 hours with the precaution that starting from a pH = 4.6 which was present at the beginning of the addition of NaOH into the reaction mixture a pH in the reaction mixture of 7.8 was not exceeded. (There was a slow pH change as in Comparison Example 1.) Twenty minutes after the beginning of the addition of the aqueous NaOH there were added a further 120 ml of water; during the last 2.7 hours of the sodium hydroxide addition the reaction mixture was held at 30° C. Then there were added within 20 minutes 46.4 grams of 49% aqueous ethylamine, then heated to 50° C and finally there were added within a further 4.7 hours another 80 grams of 25 weight % aqueous NaOH while observing the similar pH limits: 7.1–10.4 (slow pH change).

The thus obtained 2-phase reaction mixture (an aqueous-acetonic NaCl containing lower phase and a toluenic-acetonic, triazine containing upper phase) were separated warm in a separating funnel after addition of 60 grams more of acetone. The lower, aqueous phase was discarded, the upper, organic phase without further purification or subsequent treatment was evaporated to dryness in a vacuum. There were obtained 120.0 grams of a white powder which after analysis was found to consist of at least 99.8 weight % of the desired 2-(1'-cyano-1'-methylethylamino)-4-ethylamino-6-chloro-s-triazine, corresponding to a total yield of 99.5% of theory. The product contained a maximum of about 0.5 weight % of 2-(1'-cyano-1'-methylethylamino)-4-amino-6-chloro-s-triazine and no portion insoluble in acetone or methylene chloride. The triazines 2-(1'-cyano-1'-methylethylamino)-4,6-dichloro-s-triazine and 2,4-diethylamino-6-chloro-s-triazine were not detectable in the product by thin layer chromatography (detectable limit <0.1% for the first and <0.5% for the last triazine).

EXAMPLE 2

As described in Example 1, 92.2 grams of cyanuric chloride (0.5 mole) were first reacted with 0.51 mole of α-aminoisobutyronitrile and 0.5 mole of aqueous sodium hydroxide (30 weight %) at 10° C and then at 30° C and then reacted with 0.5 mole of aqueous ethylamine (50 weight %) and 0.5 mole of aqueous sodium hydroxide (30 weight %) at 50° C, with the difference that the cyanuric chloride was employed in the reaction in a solution of 830 grams of a solvent mixture consisting of 75 weight % toluene and 25 weight % acetone.

There were obtained 120 grams of a dry, white final product consisting of 2-(1'-cyano-1'-methylethylamino)-4-ethylamino-6-chloro-s-triazine having a purity of 99.5% (balance: traces of 2-(1'-cyano-1'-methylethylamino)-4-amino-6-chloro-s-triazine; 2,4-diethylamino-6-chloro-s-triazine and 2-(1'-cyano-1'-methylethylamino)-4,6-dichloro-s-triazine were not detectable by thin layer chromatography). The yield corresponds to 99.2% of theory.

EXAMPLE 3

As described in Example 1, 92.2 grams of cyanuric chloride (0.5 mole) were first reacted with 0.51 mole of α-aminoisobutyronitrile and 0.5 mole of aqueous NaOH (40 weight %) and then with 0.5 mole of aqueous ethylamine (70 weight %) and 0.5 mole of aqueous NaOH (40 weight %), however, with the difference that there was used as the solvent for the cyanuric chloride 830 grams of a mixture consisting of 85 weight % toluene and 15 weight % acetone and that the reaction with α-aminoisobutyronitrile was carried out during the first two hours of the NaOH addition at 15° C and during a further 3.5 hours the NaOH addition was at 35° C and the reaction with ethylamine in the second reaction step was carried out at 60° C.

There were obtained 119 grams of a white end product which according to the results of the analytical investigation contained at least 98.3% of 2-(1'-cyano-1'-methylethylamino)-4-ethylamino-6-chloro-s-triazine which only contained traces of 2,4-diethylamino-6-chloro-s-triazine (less than 0.7%) and of 2-(1'-cyano-1'-methylethylamino)-4-amino-6-chloro-s-triazine (less than 1%).

The yield of the desired product therefore was about 97% of theory.

EXAMPLE 4

As described in Example 1 there were reacted 92.2 grams of cyanuric chloride (0.5 mole) with 0.51 mole of α-aminoisobutyronitrile and 0.5 mole of aqueous, 25 weight % NaOH. Additionally, the cyanuric chloride was employed dissolved in 830 grams of a mixture consisting of 70 weight % toluene and 30 weight % acetone and the α-aminoisobutyronitrile was dropped in at 10° C within 20 minutes. The 140 ml of water was added and next a further steady slow addition of 80 grams of the NaOH solution so that the pH of the reaction mixture from the initial value of 4.0 gradually rose to 7.5 and the total amount of NaOH was added after 3 hours. During the last hour of the NaOH addition the temperature of the reaction mixture was raised to 25° C. Then inside 30 minutes there were added 57.1 grams of 50 weight % aqueous solution of cyclopropylamine. Then the temperature of the reaction mixture was increased to 50° C and there were dropped in a further 80 grams of 25 weight % aqueous NaOH within 3 hours, so that the pH of the reaction mixture increased from the initial 7.2 to a final value of 10.7. Then the reaction mixture obtained was worked up in the manner set forth above through separation of the aqueous-acetonic phase and collecting the crystals separating directly from the organic phase by cooling and also after evaporation of the solvent. The solid product obtained was dried in a vacuum at 60° C. There were obtained 124.6 grams of product which after the results of an analytical investigation was found to be 98.9% of 2-(1'-cyano-1'-methylethylamino)-4-cyclopropylamino-6-chloro-s-triazine, corresponding to a yield of 99.7% of theory.

EXAMPLE 5

As described in Example 1 there were reacted 92.2 grams of cyanuric chloride (0.5 mole) with 0, 52 mole of ethylamine (employed as 50% per weight aqueous solution) and 0.5 mole of aqueous, 25 weight % NaOH. Additionally, the cyanuric chloride was employed dissolved in 830 grams of a mixture consisting of 65 weight % xylene and 35 weight % methylisobutylketone and the ethylamine-solution was dropped in at 0° C within 20 minutes. The 140 ml of water was added and next a further steady slow addition of 80 grams of the NaOH solution so that the pH of the reaction mixture from the initial value of 4.0 gradually rose to 7.5 and the total amount of NaOH was added after 3 hours. During the last hour of the NaOH addition the temperature of the reaction mixture was raised to 25° C. Then inside 30 minutes there were added further 0.5 mole of ethylamine (as aqueous solution). Then the temperature of the reaction mixture was increased to 40° C and there were dropped in a further 80 grams of 25 weight % aqueous NaOH within 3 hours, so that the pH of the reaction mixture increased from the initial 7.2 to a final value of 10.7. Then the reaction mixture obtained was worked up in the manner set forth above through separation of the aqueous-ketonic phase and collecting the crystals separating directly from the organic phase by cooling and also after evaporation of the solvent. The solid product obtained was dried in a vacuum at 60° C. There were obtained 100, 83 grams of product which after the results of an analytical investigation was found to be 99,9% of 2,4-Bisethylamino-6-chloro-s-triazine, corresponding to a yield of 99,9% of theory.

The process can comprise, consist essentially of or consist of the steps set forth using the materials set forth.

What is claimed is:

1. A process for the successive substitution of two chlorine atoms of cyanuric chloride comprising reacting the cyanuric chloride with two amines in the presence of an acid binding agent and an organic solvent to produce a triazine of the formula

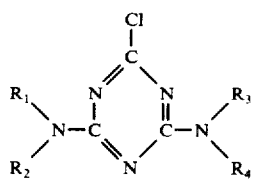

where $R_1$ and $R_2$ are lower alkyl, lower alkenyl, cyclo lower alkyl or methylcyclopropyl or such groups substituted by —OH, —OR$_5$, —SR$_5$ or CN where R$_5$ is lower alkyl with the proviso that one of $R_1$ and $R_2$ can be hydrogen, $R_3$ is as defined for $R_1$ or

and $R_4$ is

wherein $R_6$ and $R_7$ are alkyl or alkenyl of 1 to 8 carbon atoms, or together with the adjoining carbon atom form a 5 to 7 membered cycloalkyl ring or are cycloalkyl with the proviso that one of $R_6$ and $R_7$ can be hydrogen, said process comprising adding a first amine of the formula

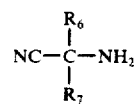

to a 4 to 60 weight % solution or suspension of cyanuric chloride in a mixture of (a) 65 to 85 weight % of a hydrocarbon solvent selected from the group consisting of an aliphatic hydrocarbon having 5 to 10 carbon atoms, a cycloaliphatic hydrocarbon having 5 to 10 carbon atoms or an aromatic hydrocarbon, and (b) 35 to 15 weight % of a ketone having 3 to 8 carbon atoms and then adding a different amine having the formula

2. A process according to claim 1 wherein the first amine is a cyanoalkylamine and the second amine is an alkylamine having 1 to 4 carbon atoms, cyclopropyl amine or methylcyclopropylamine.

3. A process according to claim 2 wherein the cyanoalkylamine is α-aminoisobutyronitrile.

4. A process according to claim 3 wherein the second amine is ethylamine or cyclopropylamine.

5. A process according to claim 4 wherein the second amine is ethylamine.

6. A process according to claim 4 wherein the second amine is cyclopropylamine.

7. A process according to claim 1 wherein the solvent mixture contains 65 to 75 weight % of the hydrocarbon and 35 to 25 weight % of the ketone.

8. A process according to claim 1 wherein the hydrocarbon is benzene, toluene, ethylbenzene or xylene or a mixture thereof.

9. A process according to claim 8 wherein the hydrocarbon is toluene and the ketone is acetone.

10. A process according to claim 1 wherein the reaction is maintained at 0° to 40° C in the reaction with the first amine and the pH at 2 to 8.5 and the reaction is maintained in the reaction with the second amine at 40° to 70° C and the pH at 6 to 11.5.

11. A process according to claim 10 wherein the reaction with the first amine is initially at 5° to 18° C and the pH is maintained at 4 to 8 and the reaction with the second amine is at 45° to 60° C and the pH at 6 to 11.0.

12. A process according to claim 1 wherein $R_1$ and $R_3$ are both hydrogen.

13. A process according to claim 12 wherein one of $R_6$ and $R_7$ is alkyl or alkenyl having 1 to 8 carbon atoms and the other is hydrogen, alkyl or alkenyl having 1 to 8 carbon atoms and wherein $R_6$ and $R_7$ together with the adjoining carbon atom may form a 5 to 7 member cycloalkyl ring.

* * * * *